United States Patent [19]

Garman et al.

[11] Patent Number: 4,609,547

[45] Date of Patent: Sep. 2, 1986

[54] ANTI-ALLERGIC COMPOSITIONS AND THEIR USE

[75] Inventors: Andrew J. Garman, Betchworth; Alan Wheeler, South Holmwood, both of England

[73] Assignee: Beecham Group p.l.c., England

[21] Appl. No.: 603,666

[22] Filed: Apr. 26, 1984

Related U.S. Application Data

[63] Continuation of Ser. No. 254,373, Apr. 15, 1981, abandoned.

[30] Foreign Application Priority Data

Apr. 15, 1980 [GB] United Kingdom ............... 8012294

[51] Int. Cl.[4] ................... A61K 39/385; A61K 39/36
[52] U.S. Cl. ........................................ 424/88; 424/91
[58] Field of Search ............................. 424/88, 91

[56] References Cited

U.S. PATENT DOCUMENTS 3,619,371  11/1971  Crook et al. ................... 424/88
4,152,411   5/1979  Schall ............................ 436/800

*Primary Examiner*—Sam Rosen
*Attorney, Agent, or Firm*—Jacobs & Jacobs

[57] ABSTRACT

Pharmaceutical compositions are described for anti-allergy therapy comprising an allergen or allergen extract, polysarcosine having an average molecular weight in the range of 2,000 to 12,000 and a chemical linking group connecting a reactive site on the polysarcosine to an amino group on the allergen or allergen extract, the reactive site on the polysarcosine being a $H(CH_3)N-$, the allergen extract being an extract from an allergen selected from pollens, weeds, house dust mites and venoms, and the chemical linking group having the formula $-CO-B-CO$ where B is a hydrocarbon chain of 1–4 carbon atoms. The disclosure also describes the analogous conjugates.

15 Claims, No Drawings

ANTI-ALLERGIC COMPOSITIONS AND THEIR USE

CROSS-REFERENCE

This is a continuation of Ser. No. 254,373 filed Apr. 15, 1981 now abandoned.

This invention relates to modified allergens, to a process for their preparation, and to their use in the therapy of allergic humans.

Many people are allergic to allergenic materials such as pollens, weeds and house dust. Such allergies have been conventionally treated by the administration to the sufferer of repeated gradually increasing doses of the relevant allergen, to build up resistance to the allergen. This is known as desensitisation.

In our U K Pat. No. 1 282 163 is described one improved form of therapy, in which the allergenicity of a given allergen is reduced by treatment with glutaraldehyde. It is found that such material maintains its ability to stimulate the desired blocking antibody, and thus may be used in desensitisation therapy with a reduced risk of side effects.

An alternative approach to the problem is the modification of the allergen such that on administration it suppresses the production of IgE antibodies specific to the unmodified allergen. Such an approach is described in Dutch Patent Application No. 7 709 025 (now also published as U.K. Pat. No. 1 578 348), wherein it is stated that allergen-polyethylene glycol conjugates are capable of eliciting the therapeutically desirable effect of suppressing in particular allergen specific IgE production. These materials are also stated to be substantially non-allergenic and non-immunogenic.

It should be noted that although in this Dutch Patent Application it is suggested that other polymers such as polyvinylalcohols, polyvinylpyrrolidones, polyacrylamides and homopolymers of amino acids may be used in place of polyethylene glycol, only polyethylene glycols are illustrated.

We have now discovered that allergens modified with polysarcosine have the ability to suppress the production of IgE antibodies specific to unmodified allergen.

Nowhere in the Dutch Patent Application referred to above is the use of this one specific material, polysarcosine, in any way disclosed or suggested.

Accordingly the present invention provides an allergen having bound thereto polysarcosine.

The allergen will be in the form of an extract of whole allergen, as is conventional. Suitable whole allergens from which the extract can be obtained include pollens, such as grass pollens, for example rye; weeds, such as ragweed; house dust mites; venoms, such as bee venom. Often the whole allergen will be ragweed, or a mixture of grasses, preferably a mixture of grasses.

The techniques for binding molecules to allergens are well known to the skilled worker, and are illustrated for example in the Dutch Patent Application. Basically, the binding depends on reacting active groups on allergen molecules with active groups on the polysarcosine, and if necessary or convenient providing such active groups as a first step.

While any appropriate known technique may of course be employed, we have found that 2,4-dichloro-6-methoxy-s-triazine is a most useful binding agent. In such cases, the bridges formed between allergen and polysarcosine may be represented by formula (I):

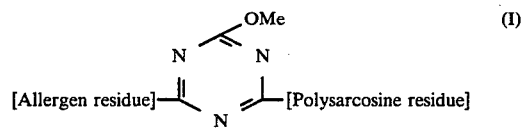

Other suitable bridges between the allergen and the polysarcosine may be represented by formula (II):

wherein B is a hydrocarbon chain of 1 to 4 carbon atoms, optionally containing a double bond. Examples of such bridges include —CO—CH$_2$—CO—, —CO—CH$_2$—CH$_2$—CO—, and —CO—CH=CH—CO—.

The binding group is suitably joined to an amino group on the allergen, and to a H(CH$_3$)N— group on the polysarcosine.

The polysarcosine for use in this invention may have any convenient molecular weight. However we have found that polysarcosine of molecular weight in the range 2000 to 12,000 is suitable, more suitably 3000 to 9000, most suitably 4000 to 8500. It has been found that a molecular weight of 7500 to 8500 is particularly useful. Polymers of molecular weight in this range are commercially available, but of course can be synthesised in conventional manner if desired or necessary. When used herein in relation to polysarcosine, molecular weights are number average molecular weights.

It will be appreciated by the skilled man that each allergen molecule will have a number of suitable sites for binding of polysarcosine molecules. It will be a routine matter for the skilled man, now that we have discovered the advantages obtained thereby, to determine by simple experiment suitable binding levels for different allergens and different molecular weight polysarcosines to give the desired activity (IgE suppression). However, by way of illustration we have found that suitably 1 to 70% of the allergen sites are bound. More suitably 4 to 40% of the sites are bound. The level of site binding is easily determined, for example as illustrated hereafter in the Examples.

From the above it will be appreciated that preferred materials of this invention include those wherein the allergen is mixed grasses, the polysarcosine has a molecular weight of 7500–8500, the bridge between allergen and polysarcosine is formed by 2,4-dichloro-6-methoxy-s-triazine, and 4 to 40% of the allergen sites are bound.

Modified allergens according to this invention may, depending on for example the allergen, polysarcosine, and degree of binding, have a significant level of retained allergenicity (as well as the necessary IgE suppression activity). Such allergens form a useful class of materials within the invention. By way of example, which is not to be taken as limiting in any way, such materials may suitably have an allergenicity not less than 10% of the unmodified allergen.

In the art, materials consisting of allergens having bound thereto chemicals, such as for example the materials described in the said Dutch Patent Application, are often referred to as 'conjugates'. Using this terminology, the materials of the present invention can be referred to as a conjugate of an allergen and polysarcosine.

The materials of this invention suppress IgE production specific to the unmodified allergen. They may therefore be used in the therapy of allergy in humans. For example, if a patient is allergic to ragweed, then a material according to this invention in which the allergen is ragweed would be used.

The materials of the present invention may be employed as the active agents in compositions such as vaccines. Such compositions are well known to those skilled in the art and comprise a sterile liquid vehicle in which the active agent is dissolved or suspended. If suspended, the particles of active agent should be small enough not to block the orifice of an injection needle. Certain additives such as tyrosine are often included in such compositions and are believed to provide a support and prolonged slow release of active material in vivo.

Usually a patient receiving treatment with such a composition is administered a number of injections, spread over a period of weeks or days.

It is also believed that the materials of the invention may be active via other routes of administration, such as the nasal mucosa, when administration can be as a liquid spray or as a dry powder.

Accordingly in an additional aspect the invention provides a pharmaceutical composition comprising a material of the invention together with a pharmaceutically acceptable carrier.

A preferred composition of this invention is as a vaccine.

The composition of this invention may, by way of illustratin, suitably contain 1 to 10000 P.N.U. of modified material.

Normally of course doses towards the lower end of this scale will be more suitable for early in the therapy; doses towards the higher end of this scale for later in the therapy.

The invention also provides a process for the preparation of the materials of this invention, which process comprises binding the polysarcosine to the allergen.

The binding reaction can be carried out in any suitable manner, following long established procedures.

For example, the polysarcosine may first be reacted with a compound D-X-E wherein X is a bridging group, and E is a group reactive with a group on polysarcosine and D is a group reactive with a group on the allergen.

One suitable example of a compound D-X-E is 2,4-dichloro-6-methoxy-s-triazine (DCMT).

Alternative examples of D-X-E include compounds wherein X is as previously defined for B, and D and E are carboxyl groups. In such cases of course E may if necessary be activated prior to reaction with the polysarcosine, and D may if necessary be protected during this reaction. Other examples of D-X-E include cyclic anhydrides.

The thus formed D-X- polysarcosine may then be bound to the allergen.

This reaction is suitably carried out in common alkaline buffer systems, for example 0.1M $Na_2CO_3$/$NaHCO_3$, pH 9.0, using a protein concentration of typically 10 mg/ml. Reaction is usually carried out at 30° C. for 1 to 3 days. Unreacted polysarcosine may suitably be separated by gel filtration using Sephadex G75 or by other convenient methods, such as ion exchange chromatography.

The degree of allergen substitution in the reaction can generally be controlled by addition of different amounts of activated polysarcosine.

The following Examples illustrate the invention.

EXAMPLE 1

(i) Preparation of DCMT

Cyanuric chloride (Aldrich, 22.08 g, 0.12 mole) was added to a mixture of methanol (120 ml), water (15 ml) and sodium bicarbonate (20.16 g, 0.24 mole). The reaction mixture was stirred at 30° C. for 30 minutes by which time $CO_2$ evolution had ceased. Water (80 ml) was added and the mixture stirred for 5 minutes. The white solid was filtered off and dried over $P_2O_5$. The product was then twice recrystallised from cyclohexane. Yield 10.3 g. m.p. 89°-90° C. (lit. 88°-90° C.) 'H-N.m.r. ($CDCl_3$): δ, 4.17 (s, 3H, $OCH_3$). Element analysis: N, 23.33 (23.30); C, 26.66 (26.65); H, 1.66 (1.35); Cl, 39.44 (39.86).

(ii) Preparation of DCMT-activated Polysarcosine$_{4800}$

Polysarcosine (Miles, No. average mol. wt ($\overline{M}_n$)=4,800, 950 mg) was dissolved in distilled water (3.3 ml) and acetone (3.3 ml) added. The pH was adjusted to 7.0 2,4-Dichloro-6-methoxy-s-triazine (114 mg 3-fold molar excess) was added with stirring, and the pH maintained at 7.0 by addition of 0.5M NaOH from an autoburette; 0.82 ml was consumed by the reaction (theoretical=0.79 ml). Undissolved DCMT crystals were removed by centrifugation and the supernatant applied to a column of Sephadex G25 SF (180 ml) equilibrated with distilled water. The peak eluting in the excluded volume of the column was pooled and the activated polysarcosine recovered by lyophilisation. Yield 637 mg. N; 18.10, 19.14 (19.88); C: 46.12, 45.90 (49.92); H, 6.81, 6.56 (6.86); Cl; (0.84, 0.82 (0.71). Calculated values assume M.W. 4,800 and that the product is anhydrous.

(iii) Preparation of Rye/Poly-Sar$_{4800}$

Rye grass pollen extract (25 mg) was dissolved in 2.5 ml 0.1M $NaHCO_3Na_2CO_3$ buffer pH 9.7 (9.5 at 37° C.) containing 0.02% $NaN_3$. DCMT-activated poly-Sar was added as shown in Table 1, Samples 1, 2, 3 and 4. Reaction was allowed to proceed for 3 days at 37° C. after which each reaction was stored frozen prior to chromatography. To each reaction mixture was added 8M KSCN in PBS (2.5 ml) and the solution was subjected to gel filtration upon a Sephadex G75 column equilibrated with 4M KSCN in PBS. To the control was added 8M KSCN in PBS (2.5 ml) followed by 4M KSCN in PBS (10 ml); this solution was allowed to stand at room temperature for ca. 4 hours. The peak eluting in the excluded volume was pooled, dialysed against 30 mM $NH_4HCO_3$ and lyophilised.

(iv) Analysis of Allergen/Poly-Sar

Allergen primary (1°) amino groups were assessed by a standard assay using trinitrobenzene sulphonic acid; the sarcosine content of the conjugates was measured by amino acid analysis; and then the corresponding number of primary amino groups of the allergen modified with polysarcosine was calculated. The degree of polysarcosine substitution was expressed as a percentage of allergen primary amino groups modified, as shown in Table 1 following.

(v) Results

The results obtained are shown in Table 1, Example 1.

EXAMPLE 2

(i)

Polysarcosine$_X$ (where X=$\overline{M}_n$) obtained from a commercial* source was activated by reaction with DCMT as described in Example 1, (ii)
[*Miles or Sigma]

(ii) Preparation of Rye/polysarcosine$_X$ conjugates

Rye-grass pollen extract (30 mg) was dissolved in 0.1MNaHCO$_3$/Na$_2$CO$_3$ buffer (pH 9.0, 3 ml) and DCMT-activated polysarcosine$_X$ (proportions shown in Table 1) added. After 20 hours at 30° each reaction mixture was frozen prior to chromatography.

The pH of the mixture was brought to 7 and 8M potassium thiocyanate in PBS added (3 ml). This solution was applied to a Sephadex G75 column equilibrated with 4M KSCN in PBS. Elution with 4M KSCN/PBS afforded separation of the conjugate, fractions of which were pooled, dialysed against 10 mmole NH$_4$HCO$_3$ until no more SCN$^{\ominus}$ ions could be detected, and lyophilised.

The buffer control was adjusted to pH 7, diluted with an equal volume of 8M KSCN/PBS and allowed to stand for 4 hours before dialysis and lyophilisation.

The products were analysed by the methods described in Example 1 (iv).

Sample Nos. 5–13 (Table 1).

EXAMPLE 3

(i) Preparation of Sarcosine-N-carboxyanhydride (Sar NCA)

Phosgene was bubbled through a solution of sarcosine (16 g, 0.18 mole) in redistilled dioxan (600 ml, dried prior to use over 3A molecular sieves) until saturation was achieved (approx. 1 hour). The solution was heated at 60°–80° for 30 mins and then stirred at room temperature for 16 hours while nitrogen was bubbled through it. Dioxan was removed under reduced pressure and the residue triturated with diethyl ether (2×100 ml). Recrystallisation from chloroform gave Sar NCA 8.52 g, 41% of theoretical.

(ii) Preparation of polysarcosine$_{6500}$

Sar NCA (1.1 g, 9.56 mmole) was dissolved in dry, redistilled pyridine (98 ml) and distilled water (20 mg) added. The solution was stirred at room temperature for 96 hours, pressure being relieved via a calcium chloride drying tube. Excess diethyl ether was added and the precipitated material filtered, washed with diethyl ether then dissolved in water and lyophilised. Yield=0.454 g, 73% theoretical of $\overline{M}_n$=6,500 (determined by an end-group titration).

This material was activated by reaction with DCMT as described in Example 1 (ii); the DCMT-activated polysarcosine$_{6500}$ thus obtained was conjugated with Rye extract as described in Example 2 (ii).

Sample Nos. 14–16 (Table 1).

EXAMPLE 4

(i)

Sar NCA (2 g, 22.5 mmole), prepared as described in Example 3 (i) was added to a solution of sarcosine (0.63 mg) in redistilled N,N-dimethylformamide and stirred at room temperature for 24 hours. Excess diethyl ether was added and the precipitated product collected by filtration, washed with diethyl ether and dissolved in water. This solution was passed down a Sephadex G15 column using water as eluant. The fractions containing polysarcosine were pooled and lyophilised to give a white solid, yield=0.785 g, 87% theoretical of $\overline{M}_n$=3400.

This material was reacted with DCMT in the manner described in Example 1 (ii) and the product conjugated with Rye-grass pollen extract as described in Example 2 (ii).

Sample No. 17 (Table 1).

EXAMPLE 5

(i) Preparation of N-phenylmethoxycarbonylsarcosine (ZSarOH)

Sarcosine (8.9 g, 0.1 mole) was dissolved in 5N NaOH (100 ml) and the solution cooled to 0° C. Benzylchloroformate (35 g, 0.2 mole) and 5N NaOH (20 ml) were added alternately, dropwise, over twenty minutes and the reaction mixture was stirred for a further three hours at room temperature.

The basic aqueous solution was washed with diethyl ether (3×80 ml), acidified to pH 4 and extracted with chloroform (3×100 ml). The combined chloroform extracts were dried over MgSO$_4$ and the solvent removed under reduced pressure to leave ZSarOH as a colourless oil (20.1 g, 88%).

H-nmr: CDCl$_3$+TMS, $\delta$, 9.9 (s, 1H, COOH), 7.3 (s, 5H, Ph), 5.2 (s, 2H, PhC$\underline{H}_2$O), 4.1 (s, 2H, NCH$_2$), 3.0 (s, 3H, NCH$_3$).

(ii) Preparation of Sarcosine-N-carboxyanhydride (SarNCA)

ZSarOH (4.0 g, 17.9 mmole) was dissolved in sodium-dried diethyl ether (25 ml) and phosphorus tribromide (2 g, 7.4 mmole) added over ten minutes. After stirring for sixteen hours, petroleum ether (bpt, 40°–60°) (100 ml) was added and the reaction mixture cooled to 4° C. for four hours to aid crystallisation. The white crystalline solid which separated was collected, washed copiously with petroluem ether, recrystallised from ethyl acetate/petroleum ether at −78° C. and stored in vacuo over phosphorus pentoxide.

Yield (1.45 g, 70%).

M.pt. 102°–104° C. (dec).

'H-nmr: CDCl$_3$+TMS, $\delta$ 4.1 (s, 2H, —CH$_2$—), 3.0 (s, 3H, NCH$_3$).

Petroleum ether and ethyl acetate were dried over molecular sieves (3A) prior to use.

(iii) Preparation of polysarcosine$_X$

N,N-Dimethylformamide (DMF) was distilled from benzene-1,3-dicarboxylic acid and sequentially dried over three batches of 3A molecular sieves. The glassware used in the reaction was baked for 48 hours at 130° prior to use.

Freshly recrystallised sarcosine-N-carboxyanhydride (0.46 g, 4 mmole) was dissolved in the required volume of N,N-dimethylformamide (see table below), the flask sealed with a rubber septum cap and the solution stirred at room temperature for 96 hours. The pressure due to carbon dioxide formation was lowered periodically via a calcium chloride drying tube attached to a syringe needle. Diethyl ether (3 volumes) was added and the precipitated polymer filtered off, washed copiously with diethyl ether and air-dried. The product was dissolved in the minimum volume of water necessary and desalted on a Sephadex G-15 column using water as eluant. Fractions containing the polymer were pooled and lyophilised to give the product as a white solid in greater than 75% of the theoretical yield.

| Molarity of SarNCA in DMF | No. average mol. wt. of product ($\overline{M}_n$) | | | |
|---|---|---|---|---|
| | Run No. | | | Pooled* Sample |
| | 1 | 2 | 3 | |
| 0.04 | 2350 | 2100 | 2135 | 2260 |
| 2.0 | 7580 | 7740 | 8160 | 7800 |

*Polysarcosine samples of similar $\overline{M}_n$ were pooled, lyophilised and analysed again.

(iv) Preparation of DCMT-activated Polysarcosine$_X$

Polysarcosine ($\overline{M}_n$ 2260, 900 mg) was dissolved in distilled water (3 ml) and the pH adjusted to 7.0 2,4-Dichloro-6-methoxy-s-triazine (144 mg, 2 eqs) in acetone (3 ml) was added with stirring and the pH maintained at 7.0 by the addition of 1M NaOH from an autoburette: 1.04 ml was consumed by the reaction (theoretical uptake=0.81 ml). Unreacted DCMT was removed by filtration and by subsequent diethyl ether washes (5×3 ml). The aqueous solution was desalted on Sephadex G-15 equilibrated with distilled water. The peak eluting at the excluded volume was pooled and lyophilised to give DCMT-activated polysarcosine$_{2260}$ (610 mg, 64%). % Cl; 1.57 (1.48, theoretical)

Polysarcosine$_{7800}$ was activated by reaction with DCMT in a similar fashion.

(v)

Conjugation of DCMT-activated polysar$_X$ materials prepared as described above was undertaken in a similar fashion to that in Example 2 (ii).

Sample Nos. 18-24 (Table 1).

EXAMPLE 6

(i)

Polysarcosine$_X$ prepared as described in Example 5 (iii) was reacted with DCMT by the method described in Example 5 (iv) to give the DCMT-activated polysarcosine$_X$ used below.

(ii) Preparation of Ragweed/polysarcosine$_X$ Conjugates

Ragweed pollen extract (30 mg) was dissolved in 0.1M NaHCO$_3$/Na$_2$CO$_3$ buffer, pH 9.0 (3 ml). DCMT-activated polysarcosine$_X$ (amounts as shown in Table 1) was added and the reaction mixture allowed to stand at 30° C. for 22 hours. The reaction mixture was then stored frozen prior to chromatography.

0.1M Tris-HCl buffer, pH 9.3, (2 ml), was added to the reaction mixture, which was then applied to a DEAE 52 ion-exchange column equilibrated with 0.1M Tris-HCl buffer, pH 9.3. Elution of the column at this pH gave two peaks. These fractions were dialysed against 10mM NH$_4$HCO$_3$ and lyophilised. Analysis revealed these products to be unconjugated polysarcosine.

After elution of these two peaks, the eluant was changed to 0.1M Tris HCl/NaOAc buffer, pH 4.2. Elution of the column at this pH gave one peak, this fraction being dialysed against 10mM NH$_4$HCO$_3$ and lyophilised to give the ragweed/polysarcosine$_X$ conjugate.

The buffer control was subjected to the pH changes described above for times similar to those experienced by the conjugates during chromatography, then dialysed against 10 mmole NH$_4$HCO$_3$ and lyophilised.

Sample Nos. 25-31 (Table 1).

TABLE 1

Analytical Data on Allergen/PolySar Conjugates

| Sample No. | | $\overline{M}_n$ of polysarcosine$_X$ | wt. ratio of DCMT-activated pSar$_X$ extract | % 1°NH$_2$+ groups modified | μmole PolySar in product per mg allergen | Biological results see Exp. No. Table No. |
|---|---|---|---|---|---|---|
| Example 1 | 1 | 4,800 | 7/1 | 56 | 0.31 | |
| | 2 | | 2/1 | 30 | 0.17 | Exp 1, Table 2 |
| | 3 | | 0.5/1 | 29 | 0.16 | |
| | 4 | | 0/1 | 0 | 0 | |
| Example 2 | 5 | 4,800 | 7/1 | 10 | 0.05 | Exp 2, Table 2 |
| | 6 | | 0 | 0 | 0 | |
| | *7 | 2,250 | 10/1 | 22 | 0.12 | |
| | 8 | | 5/1 | 17 | 0.09 | |
| | 9 | | 2.5/1 | 14 | 0.08 | |
| | 10 | 4,470 | 7/1 | 11 | 0.06 | Exp 3, Table 2 |
| | 11 | | 3.5/1 | 7 | 0.04 | |
| | *12 | | 1/1 | 4 | 0.02 | |
| | *13 | | 0.1 | 0 | 0 | *Exp 4 Table 3 |

| Sample No. | | $\overline{M}_n$ of polysarcosine$_X$ | wt. ratio of DCMT-activated pSar$_X$ extract | % 1°NH$_2$+ groups modified | μmole PolySar in conjugate per mg allergen | Biological results see Exp. No. Table No. |
|---|---|---|---|---|---|---|
| Example 3 | 14 | 6,500 | 10/1 | 26 | 0.14 | |
| | 15 | | 3.5/1 | 13 | 0.07 | Exp 5, Table 3 |
| | 16 | | 1/1 | 4 | 0.02 | |
| Example 4 | 17 | 3,400 | 4.6/1 | 5 | 0.04 | Exp 6, Table 3 |
| Example 5 | 18 | 2,260 | 6/1 | 20 | 0.11 | |
| | 19 | | 3/1 | 15 | 0.08 | |
| | 20 | | 1/3 | 7 | 0.04 | |
| | 21 | 7,800 | 6/1 | 12 | 0.11 | Exp y, Table 4 |
| | 22 | | 2.5/1 | 9 | 0.05 | |
| | 23 | | 1/1 | 7 | 0.04 | |
| | 24 | | 0.1 | 0 | 0 | |
| Example 6 | 25 | — | 0/1 | 0 | 0 | |
| | 26 | 2,260 | 0.33/1 | 12 | 0.05 | |
| | 27 | | 0.73/1 | 25 | 0.10 | |
| | 28 | | 2.33/1 | 55 | 0.21 | |
| | 29 | 7,800 | 0.1 | 0 | 0 | |
| | 30 | | 1/1 | 15 | 0.06 | |

TABLE 1-continued

Analytical Data on Allergen/PolySar Conjugates

| 31 | 2.1/1 | 28 | 0.11 |

+Calculated from $100 \times \frac{\text{m mole PolySar per gm of product}}{\text{m mole 1°NH}_2 \text{ groups expected for allergen content of product}}$

Suppression of the Developing IgE REsponse in BDI Mice

Method

Groups of 6–8 BDI mice are all immunised intraperitoneally with 10 μg of antigen adsorbed onto 0.25 mg–1.0 mg of aluminium hydroxide gel.

On days 3, 5 and 7 the animals are injected introvenously (IV) with various amounts, usually 100 μg of the modified allergen under test, in 0.5 ml diluent, unmodified allergen or diluent (0.5 ml).

Serum is taken usually on days, 10, 17 and 24. Serum from animals is bulked in groups at each bleeding time.

The antigen specific IgE antibody in each bulked serum sample is titrated by a standard passive cutaneous anaphylaxis test in two rats using a latent period of 48 hours.

Results are expressed at $-\log_4$ or $-\log_2$ from $\frac{1}{4}$ of the last dilution giving a positive result.*

*(A result of 0 indicates a level of specific IgE below the limit of detection.)

To show suppressive activity, materials when used for treatment, must reduce IgE levels in immunised animals to lower levels than in those animals immunised and treated with diluent or unmodified antigen.

[Diluent (PBS) is Bacto-haemagglutination buffer (Difco)].

TABLE 2

Suppression of the IgE response with Polysarcosine-modified Rye pollen extract.

| Expmnt No | Treatment i.v. Material Sample No/Other | Amount μg | Rye spfic IgE-log$_4$fm$\frac{1}{4}$ |  |  |  |
|---|---|---|---|---|---|---|
|  |  |  | Day |  |  |  |
|  |  |  | 10 | 17 | 24 | 31 |
| 1 | PBS | — | 4 | 4 | 4 | 4 |
|  | Rye Pollen Extract | 100 | 4 | 2 | 2 | 2 |
|  | Buffer Cont Rye, 4 | " | 3 | 0.5 | 0.5 | 1 |
|  | 1 | " | 2.5 | 0 | 2 | 1 |
|  | 2 | " | 1 | 0 | 0 | 0 |
|  | 3 | " | 2 | 0 | 0 | 0 |
| 2 | PBS | — | 5 | 4 | 5 | — |
|  | 5 | 10 | 0 | 0.5 | 1 | — |
|  | 5 | 10 | 0 | 0.5 | 2 | — |
|  | Buffer Cont Rye, 6 | 100 | 3 | 2 | 3.5 | — |
|  | Buffer Cont Rye, 6 | 10 | 3 | 3 | 3 | — |

|  |  |  | Day |  |  |  |
|---|---|---|---|---|---|---|
|  |  |  | 17 | 24 | 45 | 60 |
| 3 | PBS | — | 4 | 5 | 8 | 6 |
|  | Rye Pollen Extract | 100 | 0 | 0.5 | 5 | 5 |
|  | Buffer Cont Rye, 13 | " | 1.5 | 4 | 6.5 | 5 |
|  | 7 | " | 0 | 0 | 3 | 0.5 |
|  | 8 | " | 0 | 0.5 | 4 | 2.5 |
|  | 9 | " | 0 | 0 | 3.5 | 0.5 |
|  | 10 | " | 0 | 0 | 0.5 | 0 |
|  | 11 | " | 0 | 0 | 2 | 3 |
|  | 12 | " | 0 | 0.5 | 3 | 4 |

TABLE 3

Suppression of the IgE response with Polysarcosine-modified Rye pollen extract.

| Expmnt No | Treatment i.v. Material Sample No/Other | Amount 1/μg | Rye spfic IgE-log$_2$fm$\frac{1}{4}$ |  |  |
|---|---|---|---|---|---|
|  |  |  | Day |  |  |
|  |  |  | 17 | 24 | 52 |
| 4 | PBS | — | 6 | 7 | 6 |
|  | Rye Pollen Extract | 25 | 2 | 3 | 3 |
|  | Rye Pollen Extract | 5 | 2.5 | 3 | 5 |
|  | Buffer Cont Rye, 13 | 25 | 2.5 | 2.5 | 2 |
|  | Buffer Cont Rye, 13 | 5 | 0.5 | 1 | 2.5 |
|  | 12 | 25 | 0 | 1 | 1 |
|  | 12 | 5 | 1.5 | 0 | 1 |
|  | 7 | 25 | 0 | 0 | 0 |
|  | 7 | 5 | 0 | 0 | 0 |

|  |  |  | Day |  |  |  |  |
|---|---|---|---|---|---|---|---|
|  |  |  | 17 | 24 | 38 | 52 | 66 |
| 5 | PBS | — | 6 | 6.5 | 6 | 6 | 5 |
|  | Rye Pollen Extract | 100 | 0 | 4 | 4 | 5 | 5 |
|  | 14 | " | 0 | 0 | 0 | 0 | 0 |
|  | 15 | " | 0 | 0 | 0 | 0 | 0 |
|  | 16 | " | 0 | 0 | 0 | 0 | 0 |

|  |  |  | Day |  |  |  |
|---|---|---|---|---|---|---|
|  |  |  | 17 | 24 | 31 | 45 |
| 6 | PBS | — | 6.5 | 5.5 | 7 | 6 |
|  | 17 | 100 | 0 | 0 | 0 | 0 |
|  | 17 | 10 | 0 | 2 | 3 | 0 |
|  | 17 | 1 | 0 | 0 | 2 | 0 |
|  | Rye Pollen Extract | 100 | 0 | 0 | 1 | 2.5 |
|  | Rye Pollen Extract | 10 | 2 | 3.5 | 3 | 4 |
|  | Rye Pollen Extract | 1 | 4.5 | 5.5 | 6 | 4 |

TABLE 4

Suppression of the IgE response with Polysarcosine-modified Rye pollen extract.

| Expmnt No | Treatment i.v. Material Sample No/Other | Amount/ μg | Rye spfic IgE-log$_2$fm$\frac{1}{4}$ |  |  |
|---|---|---|---|---|---|
|  |  |  | Day |  |  |
|  |  |  | 17 | 24 | 31 |
| 7 | PBS | — | 4 | 4.5 | 4 |
|  | Rye Pollen Extract | 100 | 0 | 1 | 3 |
|  | Buffer Cont Rye, 24 | " | 0.5 | 1.5 | 2.5 |
|  | 18 | " | 0 | 0 | 0 |
|  | 19 | " | 0 | 0 | 0 |
|  | 20 | " | 0 | 0 | 0 |
|  | 21 | " | 0 | 0 | 0 |
|  | 22 | " | 0 | 0 | 0 |
|  | 23 | " | 0 | 0 | 0 |

Discussion of Results

These results show that the modified materials of the invention have the desired activity.

Toxicity

No toxic effects were observed in these tests.

What we claim is:

1. A pharmaceutical composition for anti-allergy therapy comprising an anti-allergic amount of a material which comprises
(1) an allergen or allergen extract, (2) polysarcosine of a number average molecular weight from 2,000 to 12,000, and
(3) a chemical linking group linking a reactive site on the polysarcosine to an amino group on the allergen or allergen extract, together with a pharmaceutically acceptable carrier.

2. A composition according to claim 1 wherein the reactive site on the polysarcosine is a H(CH$_3$)N— group.

3. A composition according to claim 1 wherein the allergen extract is an extract from an allergen selected from the group consisting of pollens, weeds, house dust mites and venoms.

4. A composition according to claim 1 wherein the chemical linking group is of formula —CO—B—CO where B is a hydrocarbon chain of 1 to 4 carbon atoms.

5. A composition according to claim 4 wherein B is —CH$_2$—, —CH$_2$—CH$_2$—, or —CH=CH—.

6. A composition according to claim 1 wherein the chemical linking group is of the formula

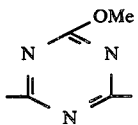

7. A composition according to claim 1 wherein the polysarcosine has a number average molecular weight in the range of 3,000 to 9,000.

8. A composition according to claim 1 wherein from 4 to 40% of available amino groups are linked to polysarcosine.

9. A composition according to claim 1 which is a liquid vaccine.

10. A composition according to claim 1 which is a liquid spray or dry powder.

11. A method for the therapeutic treatment of allergic conditions which comprises administering to an allergy sufferer an anti-allergic effective amount of a composition according to claim 1.

12. An allergen-polysarcosine conjugate which comprises
(1) an allergen or allergen extract
(2) polysarcosine of a number average molecular weight from 2,000 to 12,000,
(3) a chemical linking group of formula

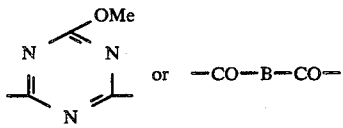

where B is a hydrocarbon chain of 1 to 4 carbon atoms, said linking group linking a reactive site on said polysarcosine to an amino grop on said allergen or allergen extract.

13. A conjugate according to claim 12 wherein B is —CH$_2$—, —CH$_2$—CH$_2$ or —CH=CH—.

14. A conjugate according to claim 12 wherein the allergen extract is an extract from an allergen selected from the group consisting of pollens, weeds, house dust mites and venoms.

15. A conjugate according to claim 12 wherein the active site on the polysarcosine is a H(CH$_3$)N— group.

* * * * *